United States Patent [19]

Hayashida et al.

[11] Patent Number: 5,593,694
[45] Date of Patent: Jan. 14, 1997

[54] SUSTAINED RELEASE TABLET

[75] Inventors: Tomohiro Hayashida; Kadoya Kikumaru, both of Chikujo-gun; Omura Tomoyuki, Takatsuki, all of Japan

[73] Assignee: Yoshitomi Pharmaceutical Industries, Ltd., Osaka, Japan

[21] Appl. No.: 211,587

[22] PCT Filed: Oct. 5, 1992

[86] PCT No.: PCT/JP92/01287

§ 371 Date: Jun. 24, 1994

§ 102(e) Date: Jun. 24, 1994

[87] PCT Pub. No.: WO93/06821

PCT Pub. Date: Apr. 15, 1993

[30] Foreign Application Priority Data

Oct. 4, 1991 [JP] Japan .................... 3-285597

[51] Int. Cl.$^6$ .............. A61K 9/22; A61K 9/32; A61K 9/36
[52] U.S. Cl. .............. 424/468; 424/464; 424/480; 424/482
[58] Field of Search .................. 424/480, 464, 424/474, 475, 479, 482, 468

[56] References Cited

U.S. PATENT DOCUMENTS

| | | | |
|---|---|---|---|
| 4,610,870 | 9/1986 | Jain et al. | 424/19 |
| 4,871,549 | 10/1989 | Ueda et al. | 424/494 |
| 4,919,938 | 4/1990 | Lovegrove et al. | 424/480 |
| 5,279,832 | 1/1994 | Greissinger et al. | 424/438 |

OTHER PUBLICATIONS

The United States Pharmacopeia, 1995, USP 23, NF 18, *Croscarmellose Sodium*, p. 2238.

*Primary Examiner*—James M. Spear
*Attorney, Agent, or Firm*—Wenderoth, Lind & Ponack

[57] ABSTRACT

A sustained release tablet comprising a base tablet comprising a water-swellable gelling agent and a pharmaceutically active ingredient dispersed homogeneously in said gelling agent, said base tablet being coated with a film coating composition prepared by dissolving one or two members selected from the group consisting of ethylcellulose and acetylcellulose in an organic solvent. The tablet is capable of zero order dissolution of both water-soluble drugs and slightly water-soluble drugs, and can be produced economically with ease.

10 Claims, 14 Drawing Sheets

―○― Example 1

―□― Comparative Example A

―◇― Comparative Example B

SUSTAINED RELEASE TABLET

TECHNICAL FIELD

This is a 371 of PCT/JP92/01287 filed Oct. 5, 1992.

The present invention relates to an orally-administered sustained release tablet showing the zero order dissolution property to maintain a constant level of concentration of a drug in blood over a long period of time.

BACKGROUND ART

Many of the pharmaceutically active ingredients currently considered useful have a short biological half life and need to be administered several times a day. Should the administration frequency of such drugs can be decreased, it will not only lessen the burden on patients but also enhance compliance of the patients and bring about higher treatment effects. For this end, it is necessary to control release of a pharmaceutically active ingredient in such a manner that an effective concentration in blood can be maintained over an extended period of time.

In this regard, release of a drug at a constant rate (zero order dissolution) irrespective of the concentration of the drug which is in the dosage form as shown in FIG. 1a will be most ideal.

Such ideal zero order drug release maintains the concentration of a drug at a constant level in the tissues, thus allowing the drug concentration in blood to stay at a safe level. In particular, this release method is most effective for a drug which causes side effects even at a concentration a drug administration can easily achieve. In addition, the administration frequency can be decreased, since efficacy of the drug can be maintained for a long time. In contrast, a dissolution with decreasing rate with time, such as that shown in FIG. 1b and presently seen in many preparations, is called a first order dissolution.

Japanese Patent Unexamined Publication No. 23814/1988 reports a sustained release pharmaceutical composition for oral administration having almost zero order release property. According to this gazette, the composition has, in the main construction, a core material comprising at least a 20% derivative cellulose as a gelling agent, a drug homogeneously dispersed in the gelling agent and optionally a pharmaceutically acceptable excipient, and a coating of a permeable, slowly-dissolving derivative cellulose polymer applied to the core material. As the gelling agent, usable is, for example, hydroxypropylmethylcellulose and as the coating polymer, usable is, for example, a dispersion of ethylcellulose (aqueous dispersion). According to the examples therein, however, the zero order release continues for the first 10 hours or up to 85% dissolution at most, and it is not verified if the dissolution remains zero order up to 100%. The reason therefor is that the ethylcellulose for the coating layer has poor binding property when used as an aqueous dispersion and the core swells as the gellation proceeds, to the point that the coating layer is finally broken.

Besides the aforementioned, there are many controlled release (sustained release) preparations being studied, such as those shown in the following.

A sustained release preparation comprising rapidly dissolving granules and slowly released granules in combination in, for example, a capsule, such as the one for rhinitis achieves the sustained release according to a preparation design in which the rapidly dissolving part is dissolved immediately after administration and then a predetermined amount of a drug is released gradually from the slowly released part. In this case, the defect is that the production of the granules to be released slowly with time should be modified every time a drug to be contained changes, as can be seen in Japanese Patent Unexamined Publication Nos. 103012/1987, 197433/1989 and 230513/1989. The release of a drug from globular sustained release granules as described does not make a zero order release, since dissolution rate slows down with time due to the decreasing concentration gradient of the drug contained in the granules, as a result of the dissolution of the drug through an outer layer without destruction of the granules. This type of preparation mostly releases drug by allowing same to dissolve through a film which is formed on a spherical granule containing the drug and which does not dissolve in a digestive juice. For this mechanism, this type of preparation cannot be applied to a drug slightly soluble in water. While there are other types of dissolution which are similar to the one mentioned above, such as simple matrix type dissolution wherein a drug is encapsulated in a wax or a water-insoluble coating agent and gradually dissolved through the outer layer or the drug is dissolved along with the dissolution of the outer layer, such preparations hardly achieve a zero order release but rather a first order release, since the drug dissolution area becomes smaller as the drug dissolves out.

The hydrophilic polymer matrix preparations recently drawing attention have a preparation design in which a drug dispersed in a hydrophilic polymer is diffused through the gel formed by the polymer by the absorption of water in the digestive tract, and released from the gel layer. For example, EP-B-282,111, Japanese Patent Unexamined Publication No. 128917/1989 and SE-A-8008646-5 disclose controlled release of a pharmaceutically active ingredient by the use of a gelling polymer. The swelling type sustained release tablets using a hydrophilic polymer comprise those wherein tablets simply absorb water, swell (into a spherical shape in this ease) and disintegrate from the outer layer where dissolution begins gradually, and those wherein a drug dissolves out beginning from the outer layer to the inner layer while maintaining the swollen, spherical shape. The significant defect is that they can be prepared into first order dissolution preparations only, since the dissolution area becomes smaller as the drug dissolves out and the concentration of the drug in the matrix develops a gradient.

When a semipermeable film, a water-swellable film such as polyacrylate or an enteric-coated film generally used for sustained release preparations is used, possible swelling is as conventional as the one shown in FIG. 3, wherein a tablet gradually absorbs water from the entire surface through the film so that it swells into a sphere, or the film is dissolved in a gastric juice so that the tablet absorbs water from the entire surface and swells into a sphere, with the result that a zero order release cannot be attained. When an enteric coating is mainly used, administration of the tablet to the patients suffering from achlorhydria may be difficult.

When using a prior art technique, formulation and production method should be greatly modified according to the characteristics of the pharmaceutically active ingredient to be administered. For example, Japanese Patent Unexamined Publication No. 1614/1986 teaches triple coating of different types of pH-dependent films to achieve sustained release. The above-mentioned Japanese Patent Unexamined Publication No. 23814/1988 teaches the use of a buffer according to the pharmaceutically active ingredient.

Besides the aforementioned, many sustained release preparations have been developed, which basically are, generally-classified, of simple matrix type inclusive of those having a hole in the coated film, of membrane permeable type to allow dissolution of a drug through a semipermeable film, of water-swellable matrix type, or of disintegration or dissolution type, and at the present moment, there has not been provided a zero order sustained release tablet which is applicable to both water-soluble and slightly water-soluble drugs.

DISCLOSURE OF THE INVENTION

The present inventors have conducted intensive studies with the aim of developing a zero order sustained release tablet applicable to both water-soluble and slightly water-soluble drugs and available for easy and economical production, and found that a tablet-specific swelling and disintegration, or dissolution property, can be imparted to the tablet and a tablet capable of zero order release of a pharmaceutically active ingredient, irrespective of whether the ingredient is water-soluble or slightly water-soluble, can be produced by applying a film coating composition prepared by dissolving ethylcellulose and/or acetylcellulose in an organic solvent to a base tablet mainly comprising a water-swellable gelling agent, which resulted in the completion of the invention.

That is, the present invention relates to a sustained release tablet comprising a base tablet containing a water-swellable gelling agent and a pharmaceutically active ingredient dispersed homogeneously in said gelling agent, said base tablet being coated with a film coating composition prepared by dissolving one or two members from ethylcellulose and acetylcellulose in an organic solvent.

DETAILED DESCRIPTION OF THE INVENTION

Figure 1:
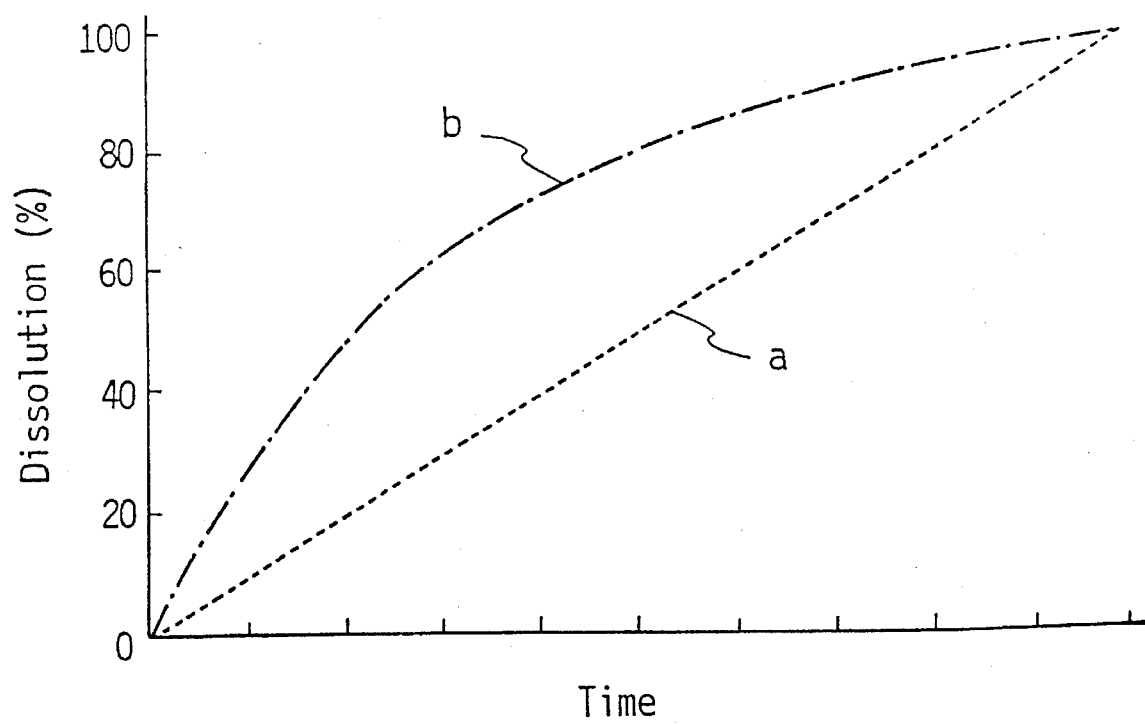
FIG. 1 shows typical patterns of zero order and first order dissolutions, wherein a is zero order type dissolution and b is first order type dissolution.

The present invention is characterized by the coating of a base tablet containing a water-swellable gelling agent, with a film coating composition prepared by dissolving ethylcellulose and/or acetylcellulose in an organic solvent, whereby a strong film which is insoluble in water and the digestive juice and resistant to a deformation such as swelling is formed.

Coating with such a film aims at tightly fixing the arc surfaces of a tablet (the upper surface and the bottom surface of a tablet) and causing swelling of the tablet with water absorbed from the side portion where the coated film is most vulnerable. More specifically, initial water absorption and release of a drug from the upper and bottom arc surfaces of a tablet are suppressed, so that water is absorbed from the side of the tablet where the film is thin to cause gellation and swelling inside the tablet to the point that the film is broken into two at the thin side surface, which allows for the specific swelling of the tablet as shown in FIG. 2, with the result that the pharmaceutically active ingredient is dissolved mostly from the exposed side alone, to achieve the zero order release of the drug.

Examples of the water-swellable gelling agent to be used for the base tablet include hydroxypropylcellulose (HPC-L, Shin-Etsu Kagaku), hydroxypropylmethylcellulose (Metolose 60SH50, 65SH1500, Shin-Etsu Kagaku), aminoacrylmethacrylate copolymer RS (Eudragit RS-PM, Higuchi Shokai), emulsion of ethyl acrylate and methyl methacrylate copolymer (Eudragit NE30D, Higuchi Shokai), pullulan, collagen, casein, agar, gum arabic, sodium carboxymethylcellulose (Cellogen F, Daiichi Kogyo Seiyaku) and methylcellulose, which may be used in combination. While the amount of the gelling agent varies depending on the properties of the pharmaceutically active ingredient to be applied, the kind of the gelling agent to be used and other additives to be combined, it is generally in a proportion of at least 10% by weight, preferably at least 20% by weight per base tablet e.g., 31.1–82.5% water-swellable gelling agent per base tablet. The film coating composition can be prepared by dissolving one or two members from ethylcellulose (ETHOCEL 10, ETHOCEL 45, DOW CHEMICAL JAPAN LTD.) and acetylcellulose in an organic solvent in a proportion of 0.5–10% by weight. Examples of the organic solvent include acetone, benzene, toluene, methylene chloride, chloroform, ethyl acetate and alcohols such as ethanol and isopropyl alcohol, which may be used in combination, or water may be added up to about 30%. The preferable film coating component is ethylcellulose and the preferable organic solvents from the viewpoint of safety are ethanol, methylene chloride and ethyl acetate. By dissolving a film coating component in an organic solvent, a strong film insoluble in water and digestive juice and resistant to a deformation such as swelling in water and digestive juice (not easily destructed with water) becomes formable.

Ethylcellulose has various grades according to viscosity and contents of ethoxy group (—OC$_2$H$_5$) in the cellulose molecule and generally used are ETHOCEL 10 and ETHOCEL 45. A film formed by ethylcellulose which is dissolved in an organic solvent is strong and resilient. In the case of ETHOCEL 10, a film coating is generally applied at a concentration of about 1–10% by weight and in the case of ETHOCEL 45, it is applied at a still lower concentration (about 0.5–8%).

Water-soluble film base material such as polyethylene glycol (polyethylene glycol 6000), hydroxypropylmethylcellulose and hydroxypropylcellulose; enteric coating agent such as polyvinylacetaldiethylaminoacetate (AEA, Sankyo) and aminoalkylmethacrylate copolymer E; permeable, swellable polymers such as aminoalkylmethacrylate copolymer RS; powders generally used for coating such as crystalline cellulose, light silicic acid anhydride, Carmellose sodium, precipitated calcium carbonate, talc, calcium stearate and magnesium stearate; and other additives for coating may be optionally used in combination, depending on the properties of the tablet and the properties of the pharmaceutically active ingredient to be contained in the tablet. It should be noted, however, that ethylcellulose and acetylcellulose, which are the main constituting components, need to be used in an amount which does not cause marked increase in swellability, stretchability, permeability and the like of the coated film, namely, in an amount which does not impair the properties of the film, preferably 50% by weight.

The sustained release tablet of the present invention is prepared by mixing a water-swellable gelling agent, a pharmaceutically active ingredient and, if necessary, additives for preparations, preparing a base tablet by a wet method or a dry method and coating the base tablet with a film coating composition prepared by dissolving ethylcellulose and/or acetylcellulose (basic components) in an organic solvent.

The film coating is generally applied to the tablet of the present invention by coating pan method conventionally used, which is preferably done by spraying automatically or manually.

The thickness of the film is an essential factor for the tablet of the present invention. Too thin a film suffers from brittleness and easy peeling so that the control of initial dissolution becomes difficult and the desired swelling cannot be achieved. On the other hand, too thick a film gives rise to problems in that semipermeability of the film is degraded, prolonged lag time in the initial dissolution leads to a poorly sustained release and the desired swelling is hindered by difficult breaking of the film at the side. The thickness of the film can be easily measured from comparing the thickness of the tablet before film coating and that after film coating, which may be done with a manually-operative or automatic thickness reader.

The sustained release tablet of the present invention preferably contains a film coating composition in a proportion of 0.5–15% by weight relative to the base tablet and has a film thickness of 0.002–0.05 mm on the side and 0.003–0.06 mm at the top and the bottom. The ratio of the film thickness on the side to that at the top or the bottom is 0.55–0.85, preferably 0.6–0.75.

The base tablet of the sustained release tablet of the present invention may optionally contain, not to mention a dissolution rate-adjusting agent conventionally used, such as polyethylene glycol, stearic acid and hydrogenated vegetable oil, excipients such as lactose, corn starch and crystalline cellulose, lubricants such as magnesium stearate and talc, binders such as starch, sucrose, gelatin, gum arabic powder, methylcellulose, sodium carboxymethylcellulose, hydroxypropylmethylcellulose and polyvinylpyrrolidone, disintegrators such as calcium carboxymethylcellulose, carboxymethylcellulose and low substituted hydroxypropylcellulose, coloring, taste-improving, adsorbent, preservative, wetting agent and antistatic agent.

While the drug release pattern is generally constant with no dependency on pH, which is achieved by selecting a suitable gelling agent, when the drug per se is pH-dependent, any problem in this regard can be solved by adding an organic acid such as fumaric acid or citric acid.

The technique of the present invention enables production of a tablet having an optional dissolution speed irrespective of whether the main pharmaceutically active ingredient is water-soluble or slightly water-soluble, by the use of a selected gelling agent and selected additives which are suitable for preparations and contribute to the dissolution property, and can be used for various pharmaceutically active ingredients having diversified fields of efficacy. Since the sustained release tablet of the present invention aims at the sustained release of a drug not through a semipermeable film but by suitably-adjusting the speed of the disintegration and dissolution from the side of the gelled outer layer, the pharmaceutically active ingredient is not restricted in number, permitting many kinds of ingredients to be contained.

The pharmaceutically active ingredient to which the preparation of the present invention can be applied may be any insofar as it benefits the patients by being slowly released, and is exemplified by, but not limited to, phenylpropanolamine hydrochloride, ethenzamide, cloperastine hydrochloride, diphenhydramine hydrochloride, procainamide hydrochloride, ephedrine hydrochloride, meclofenamate sodium, meclofenoxate hydrochloride, theophylline, caffeine, chlorpheniramine maleate, sulfanilamide, sulfisoxazole, sulfadiazine, molsidomine, valproate sodium, aspirin, trepibutone, idebenone, ketoprofen, cyclandelate, enalapril, amitriptyline hydrochloride, cyproheptadine, cyclobenzoprine, timolol, propranolol hydrochloride, betaxolol, diflunisal, ibuprofen, norfloxacin, aluminum trisilicate, alminum hydroxide, cimetidine, phenylbutazone, indomethacin naproxen, flurbiprofen, diclofenac, dexamethasone, prednisolone, glyceryl trinitrate, isosorbide dinitrate, pentaerythritol tetranitrate, naftidrofuryl oxalate, cyclandelate, nicotinic acid, erythromycin stearate, cefalexin, nalidixic acid, tetracycline hydrochloride, ampicillin, flucloxacillin sodium, hexamine mandelate, hexamine hippurate, fludiazepam, diazepam, doxepin, thioridazine, trifluoperazine, fluphenazine, piperothiazine, haloperidol, maprotiline hydrochloride, imipramine, desipramine, lithium carbonate, lithium sulfate, methylphenidate, isoproterenol, amphetamine sulfate, amphetamine hydrochloride, chlorpheniramine, profenamine, difenidol, bisacodyl, magnesium hydroxide, sodium dioctylsulfosuccinate, phenylpropanolamine, ephedrine, α-tocopherol, thiamine, pyridoxine, astorbic acid, propantheline bromide, metoclopramide, diphenoxylate, suloctidilum, naftidrofuryl oxalate, co-dergocrine mesylate, diltiazem, verapamil, disopyramide, pretium tosylate, quinidine sulfate, quinidine glueonate, procainamide, kanetydine sulfate, methyldopa, oxprenolol hydrochloride, captopril, hydralazine, ergotamine, protamine sulfate, ε-aminocaproic acid, acetaminophen, acetylsalicylic acid, oxycodone, morphine, heroin, nalbuphine, butorphanol tartrate, pentazocine, cyclazacine, pethidine hydrochloride, piprenorphine, scopolamine, mefenamic acid, dicloral fenazone, nitrazepam, temazepam, chlorpromazine, promethazine teoclate, sodium valproate, phenytoin, dantrolene sodium, diapenase, glucagon, tolbutamide, insulin, thyroxine, triiodothyronine, propylthiouraeil, furosemide, chlorthalidone, hydrochlorothiazide, spironolactone, triamterene, phentermine, diethylproprione hydrochloride, fenfluramine hydrochloride, calcium gluconate, ferrous sulfate, aminophylline, oxyprenalin sulfate, terbutaline sulfate, salbutamol, carboeisteine, guaifenesin, noscapine, codeine phosphate, codeine sulfate, dihydrocodeine tartrate, dextromethorphan, allopurinol, probenecid, sulfinpyrazone, cetylpyridinium hydrochloride, thyrothricin, chlorhexidine, carbetapentane citrate, nifedipine, pindolol, nicardipine hydrochloride, pentoxifylline, cefaclor, morphine sulfate, pranoprofen, papaverine and so on.

Figure 2A:
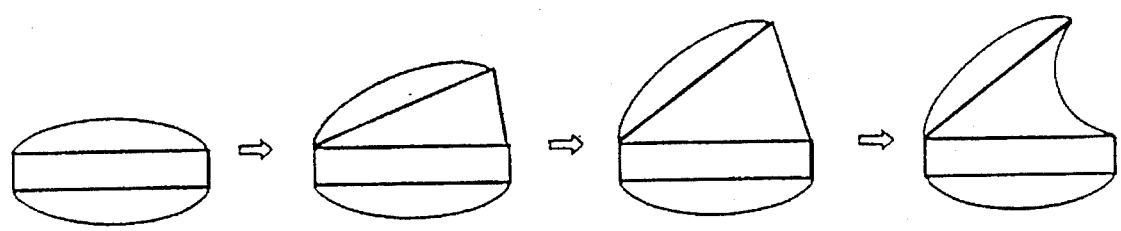
FIG. 2 shows swelling and dissolution of the tablet of the present invention, wherein (A) is a tablet swollen in a shell shape and (B) is a tablet swollen in a lantern shape.
Figure 2B:
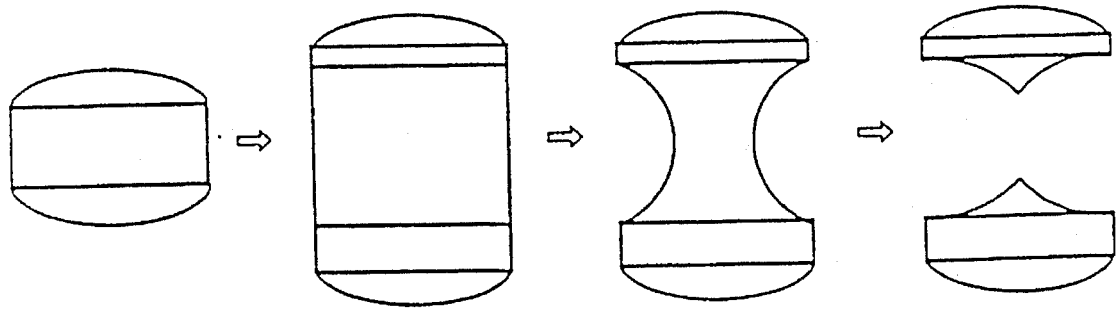

According to the present invention, a rapid release of drug is suppressed by applying a film coating composition prepared by dissolving ethylcellulose and/or acetylcellulose in an organic solvent, to a base tablet to form an initial barrier of a strong film which is insoluble in water and digestive juice and free of denaturing. Since the film has a slight permeability, water or digestive juice permeates through the film into the tablet to cause swelling and gelling of the base tablet and dissolution of a drug. The tablet becomes swollen to a higher degree with the progress of gellation caused by water absorption to finally become broken into two from the side where the film is the weakest. At this point, the tablet looks like an open shell. The tablet of the invention often proceeds further with gellation into a lantern shape. The drug is gradually diffused or dissolved into disintegration from the side exposed as a result of the gellation of the tablet or released at a constant speed through the swollen side wall, which are shown in FIG. 2(A) and 2(B). The release of a pharmaceutically active ingredient from the tablet swollen in a specific shape continues until almost 100% zero order dissolution is achieved, whether swelling results in a lantern shape or a shell shape. This is an important finding for the formulation of pharmaceutical preparations.

The time before the initiation of the dissolution (lag time) and the surge of drug release at the initial stage can be controlled by varying the thickness of the film.

Sustained release preparations are often designed such that the rapid release portion dissolves first and then the sustained release portion gradually dissolves out. Also, the tablet of the present invention may be used as a core tablet to be applied with a pharmaceutically active ingredient as the rapid release portion and easily prepared into film-coated tablets, sugar-coated tablets, compression-coated tablets (dry coated tablets) and so on, to provide an ideal sustained release tablet capable of zero order dissolution of the pharmaceutically active ingredient from the sustained release portion.

The zero order release of the pharmaceutically active ingredient by the tablet of the present invention is explained as follows.

Figure 3:
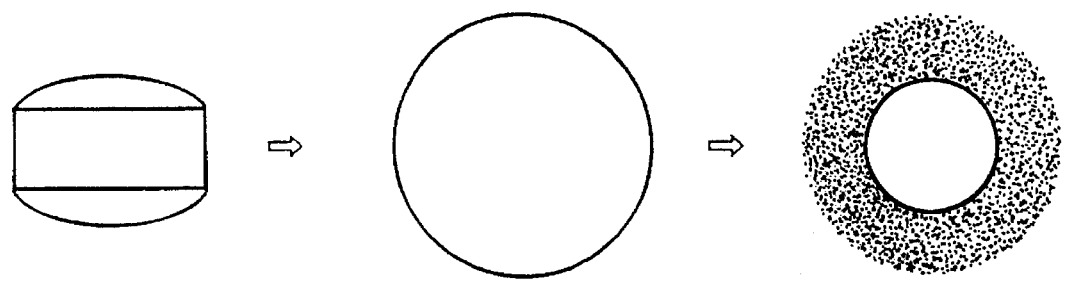
FIG. 3 shows swelling and dissolution of a conventional swellable sustained release tablet.
Figure 4:
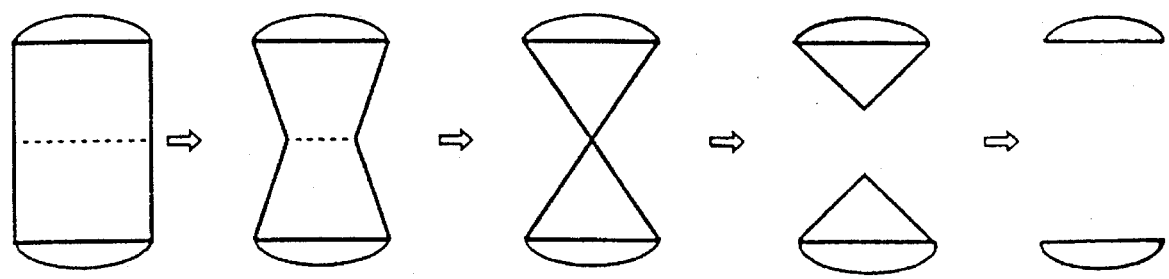
FIG. 4 shows schematic (approximate) disintegration of the tablet of the present invention which swelled like a lantern.
Figure 5:
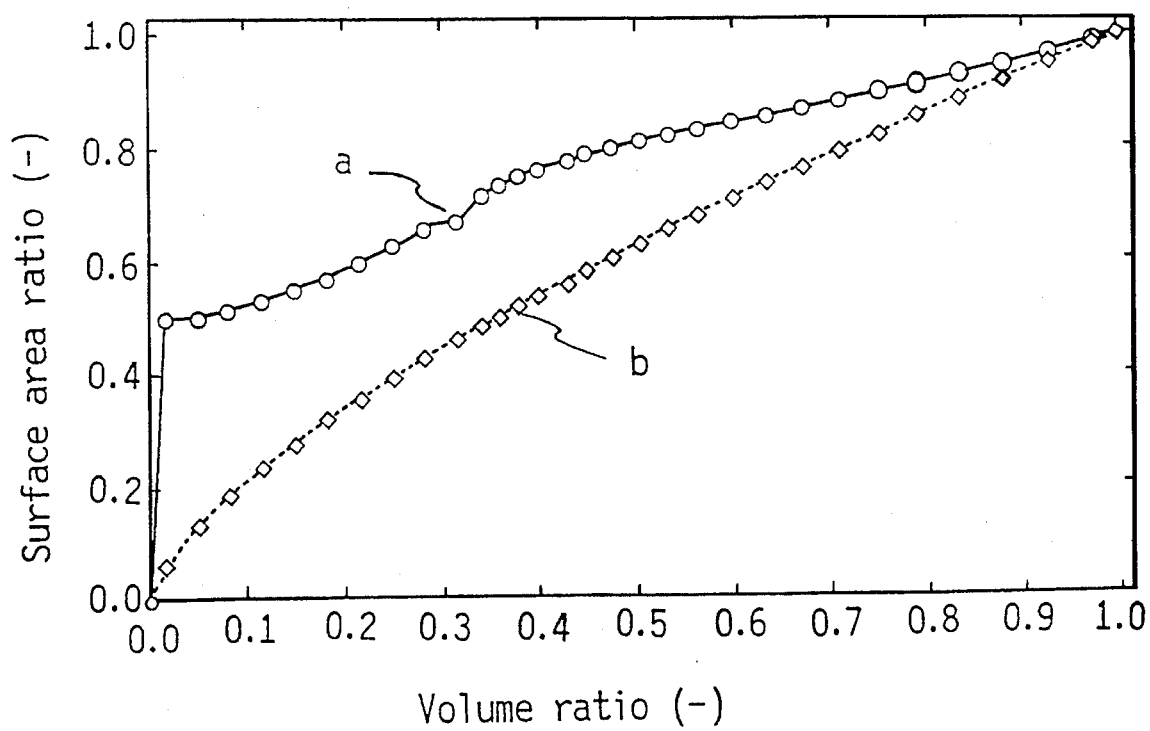
FIG. 5 shows changes in volume and surface area of the tablet which swelled like a lantern or a sphere, wherein a shows the tablet of the present invention which swelled like a lantern and b shows a conventional tablet which swelled like a sphere.

The conventional swellable sustained release tablet swells into a sphere as shown in FIG. 3 and gradually becomes smaller while retaining its shape. Assuming that the sustained release tablet of the present invention undergoes approximately the dissolution and disintegration as shown in FIG. 4 and the tablet of the present invention and the conventional swellable sustained release tablet swell to the same volume, the surface area of each tablet changes in the manner shown in FIG. 5, wherein a shows a tablet of the present invention which swelled like a lantern and b shows a conventional tablet which swelled like a sphere, as the volume decreases. As is evident from FIG. 5, the change in the surface area caused by the swelling of the tablet and dissolution of the pharmaceutically active ingredient therefrom is far smaller in the tablet of the present invention (FIG. 5, a). As a result, the pharmaceutically active ingredient is released from the tablet following the swelling manner of the present invention of a zero order type. It is undeniable that the dissolution through the film occurs with time, but it is negligibly small and has no great influence on the overall dissolution pattern. The same thing can be said about the tablet which undergoes shell shape swelling.

While many gelling preparations have been so far developed, there is no preparation such as the one according to the present invention wherein a tablet is coated with a film prepared by dissolving ethylcellulose and/or acetylcellulose in an organic solvent and having no semipermiability, to achieve specific swelling (into a lantern shape or shell shape) and specific disintegration or dissolution. According to the present invention, an ideal sustained release tablet with less time-course decrease of the drug dissolution surface area and no change in the gradient of drug concentration in the tablet is provided, with the effect that zero order release of the internally present pharmaceutically active ingredient up to 100% can be achieved.

In addition, the sustained release tablet of the present invention can achieve the zero order dissolution irrespective of whether the pharmaceutically active ingredient is water-soluble or slightly water-soluble and can be applied to the mixtures thereof, which is a significant characteristic of the invention.

Furthermore, the tablet is extremely advantageous, since it resides in the stomach for a long time for the reason that the tablet absorbs water and swells into a specific shape of a lantern or a shell after breaking at the side and that the tablet per se gelatinizes itself to become floatable. Alternatively, the tablet is a very characteristic one having many significantly beneficial aspects as a sustained release tablet, such as zero order drug dissolution and prolonged time before being discharged from the stomach.

The sustained release tablet of the invention can be prepared easily and does not need a special apparatus for its production, which is also beneficial, and ideal as a sustained release tablet.

The present invention is explained in detail by illustration of examples, to which the invention is not limited.

EXAMPLE 1

Tablet (per tablet)

| [Base tablet] | |
|---|---|
| Phenylpropanolamine hydrochloride | 37.5 mg |
| Metolose 60SH4000 | 181.6 mg |
| Magnesium stearate | 0.9 mg |
| Subtotal | 220.0 mg |
| [Film] | |
| ETHOCEL 10 | 5.0 mg |
| Polyethylene glycol 6000 | 0.5 mg |
| Subtotal | 5.5 mg |
| Total | 225.5 mg |

To phenylpropanolamine hydrochloride (187.5 g) passed through a 80 mesh sieve were added Metolose 60SH4000 (907.5 g) and magnesium stearate (4.5 g), and the mixture was thoroughly mixed. The mixture was directly compress-formed by a continuous compressor equipped with a 8 mm diameter, 6.5 R pounder under the main pressure of 1 ton into tablets each weighing 220 mg. Then, the obtained base tablets (1 kg) were placed in a pan coater (Freund Industry) and a solution of ETHOCEL 10 (90 g) and polyethylene glycol 6000 (10 g) in a mixture (2000 ml) of water-ethanol (1:9) was sprayed thereon, followed by drying to give film coated tablets.

As Comparative Examples, the same base tablet as in the tablet of the present invention but applied with a coating film (Eudragit RS-PM) permitting water-swellable deformation into a sphere (Comparative Example A) and a conventional non-swelling type sustained release tablet with a semipermeable film (Comparative Example B) were prepared.

Comparative Example A

Tablet (per tablet)

| [Base tablet] | |
| --- | --- |
| Phenylpropanolamine hydrochloride | 37.5 mg |
| Metolose 60SH4000 | 181.6 mg |
| Magnesium stearate | 0.9 mg |
| Subtotal | 220.0 mg |
| [Film] | |
| Eudragit RS-PM | 7.0 mg |
| Subtotal | 7.0 mg |
| Total | 227.0 mg |

Comparative Example B
Tablet (per tablet)

| [Base tablet] | |
| --- | --- |
| Phenylpropanolamine hydrochloride | 37.5 mg |
| Calcium citrate | 137.6 mg |
| Lactose | 44.0 mg |
| Magnesium stearate | 0.9 mg |
| Subtotal | 220.0 mg |
| [Film] | |
| ETHOCEL 10 | 13.0 mg |
| Polyethylene glycol 6000 | 9.0 mg |
| Subtotal | 22.0 mg |
| Total | 242.0 mg |

Figure 6:
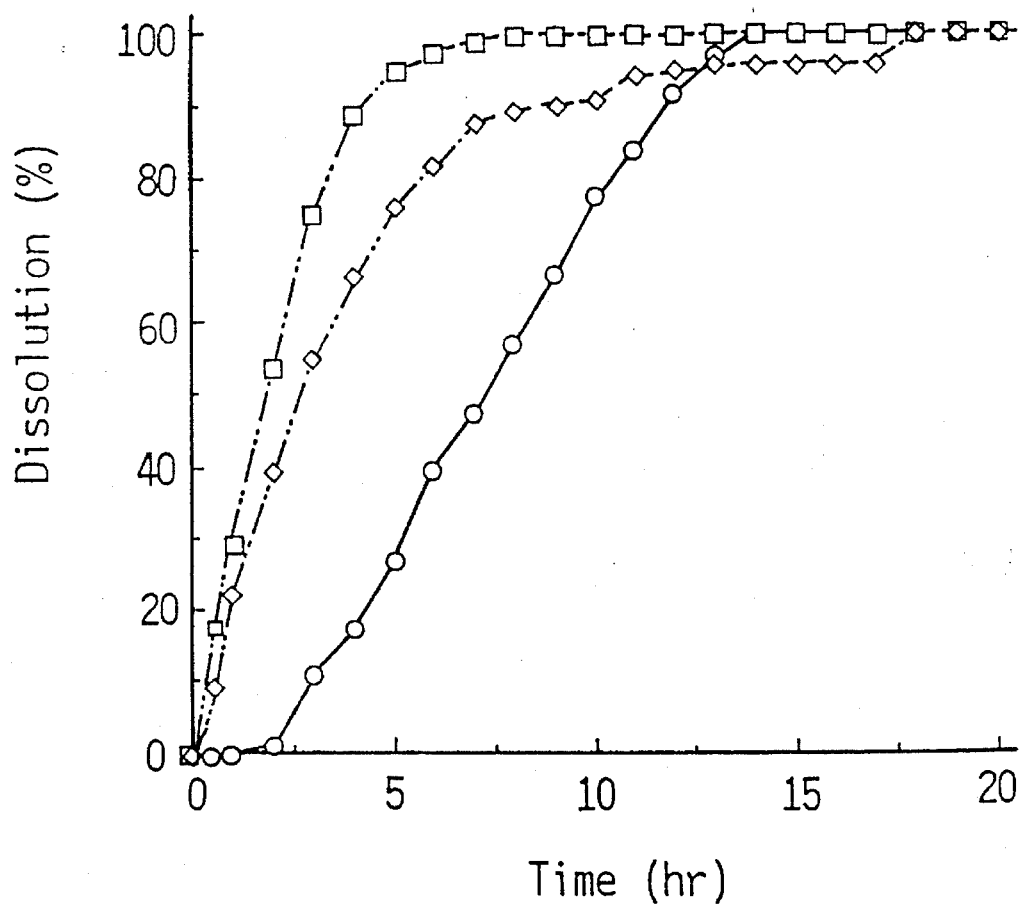
FIG. 6 is a graph showing the dissolution of the tablets of Example 1, Comparative Example A and Comparative Example B.

With regard to these film coated tablets, the dissolution test was conducted using a test apparatus according to the dissolution test method (paddle method) of the Japanese Pharmacopoeia, 11th ed., in purified water (900 ml) at 37° C. and 100 rpm paddle rotation. The results are shown in FIG. 6. The water-soluble phenylpropanolamine hydrochloride clearly showed zero order dissolution from the tablet of the present invention as compared with the tablets of Comparative Examples A and B.

EXAMPLE 2

Tablet (per tablet)

| [Base tablet] | |
| --- | --- |
| Phenylpropanolamine hydrochloride | 37.5 mg |
| Metolose 60SH50 | 45.3 mg |
| Cellogen F | 45.3 mg |
| Lactose | 88.0 mg |
| Talc | 3.0 mg |
| Magnesium stearate | 0.9 mg |
| Subtotal | 220.0 mg |
| [Film] | |
| ETHOCEL 10 | 15.0 mg |
| Polyethylene glycol 6000 | 7.0 mg |
| Subtotal | 22.0 mg |
| Total | 242.0 mg |

To phenylpropanolamine hydrochloride (187.5 g) passed through a 80 mesh sieve were added Metelose 60SH50 (226.5 g), Cellogen F (226.5 g), lactose (440 g), talc (15 g) and magnesium stearate (4.5 g), and the mixture was thoroughly mixed. The mixture was directly compress-formed by a continuous compressor equipped with a 8 mm diameter, 6.5 R pounder under the main pressure of 1 ton into tablets each weighing 220 nag. Then, the obtained base tablets (1 kg) were placed in a pan coater (Freund Industry) and a solution of ETHOCEL 10 (90 g) and polyethylene glycol 6000 (42 g) in a mixture (2600 ml) of water-ethanol (1:9) was sprayed thereon, followed by drying to give film coated tablets.

Figure 7:
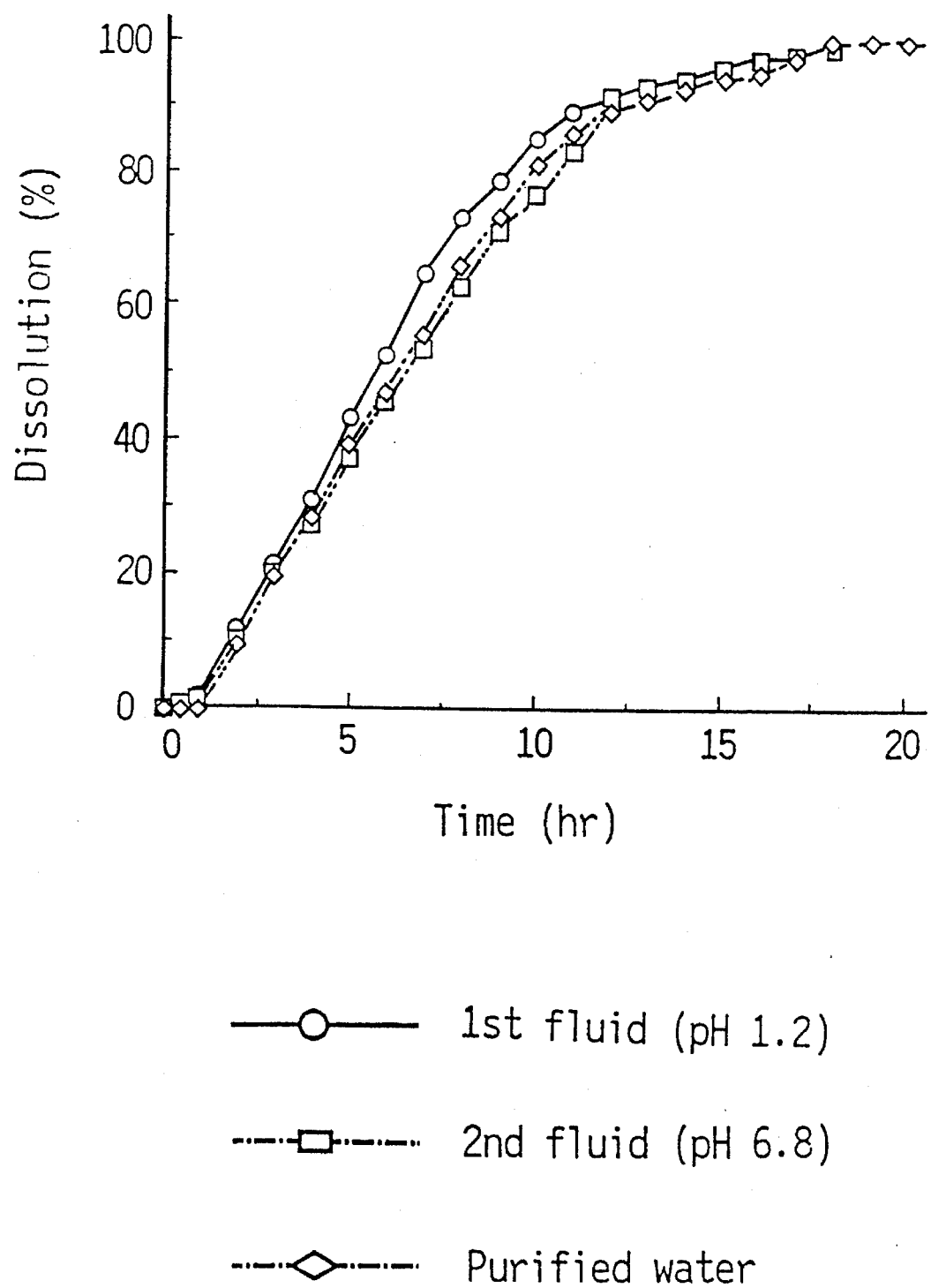
FIG. 7 is a graph showing the dissolution of the tablet of Example 2.

With regard to these film coated tablets, the dissolution test was conducted using a test vessel according to the dissolution test method (paddle method) of the Japanese Pharmacopoeia, 11th ed., in three kinds of dissolution test solutions (each 900 ml) of water at 37° C., 1st fluid (pH 1.2) and 2nd fluid (pH 6.8) and at 100 rpm paddle rotation. The results are shown in FIG. 7. The phenylpropanolamine hydrochloride clearly showed zero order dissolution in every solution and there was found no significant difference among the respective test solutions.

| [Base tablet] | |
| --- | --- |
| Acetaminophenone | 37.5 mg |
| Metolose 60SH50 | 45.3 mg |
| Cellogen F | 45.3 mg |
| Lactose | 88.0 mg |
| Talc | 3.0 mg |
| Magnesium stearate | 0.9 mg |
| Subtotal | 220.0 mg |
| [Film] | |
| ETHOCEL 10 | 15.0 mg |
| Polyethylene glycol 6000 | 7.0 mg |
| Subtotal | 22.0 mg |
| Total | 242.0 mg |

Figure 8:
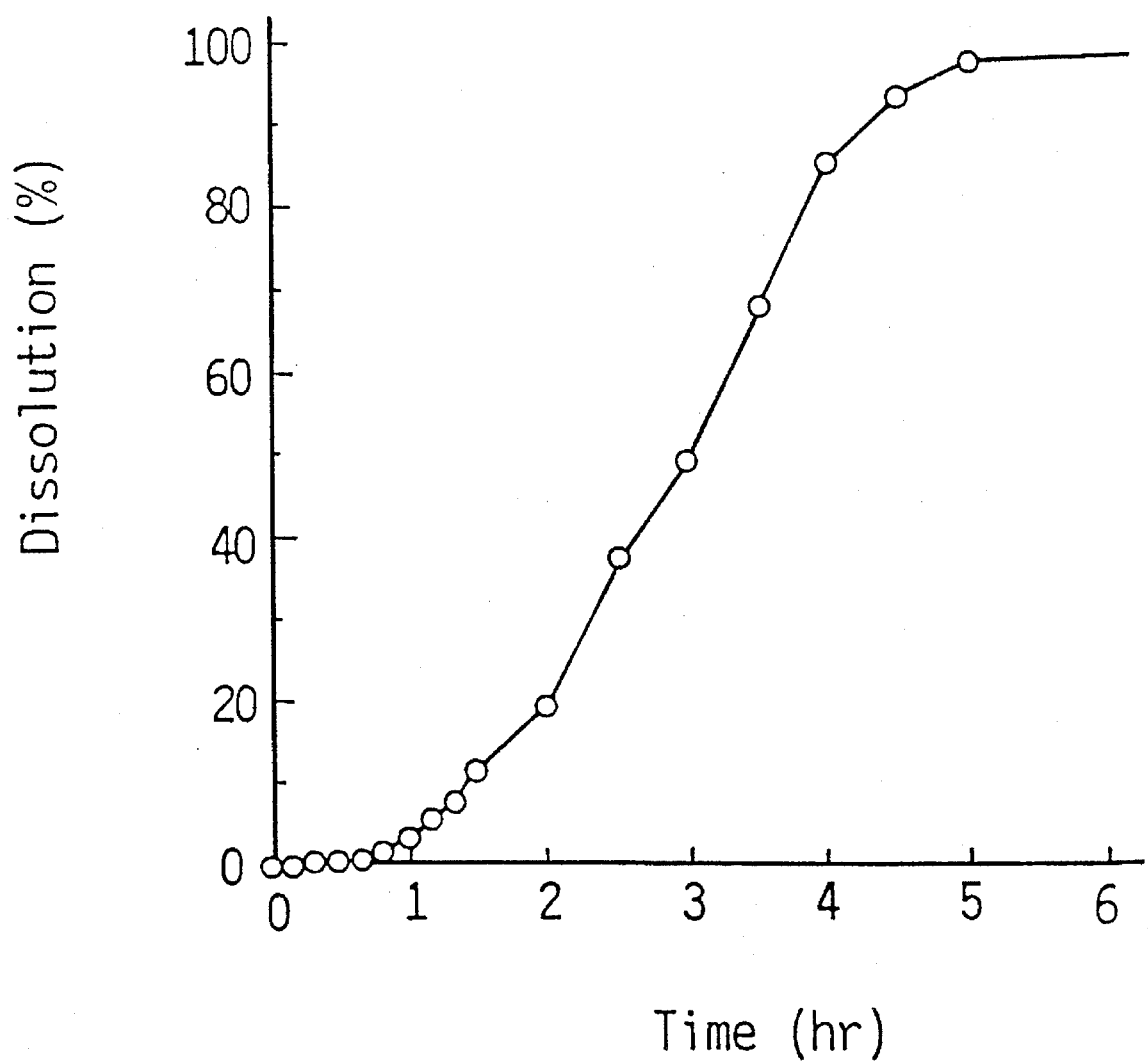
FIG. 8 is a graph showing the dissolution of the tablet of Example 3.

Using the same production method and the same dissolution test method as in Example 1, the dissolution test was conducted with water at 37° C. This examples is concerned with the application to a slightly water-soluble pharmaceutically active ingredient. As shown in FIG. 8, acetaminophene showed property of zero order dissolution.

EXAMPLE 4

Tablet (per tablet)

| [Base tablet] | |
| --- | --- |
| Ethenzamide | 18.75 mg |

-continued

| | |
|---|---|
| Cloperastine chloride | 18.75 mg |
| Metolose 60SH50 | 45.3 mg |
| Cellogen F | 45.3 mg |
| Lactose | 88.0 mg |
| Talc | 3.0 mg |
| Magnesium stearate | 0.9 mg |
| Subtotal | 220.0 mg |
| [Film] | |
| ETHOCEL 10 | 15.0 mg |
| Polyethylene glycol 6000 | 7.0 mg |
| Subtotal | 22.0 mg |
| Total | 242.0 mg |

Figure 9:
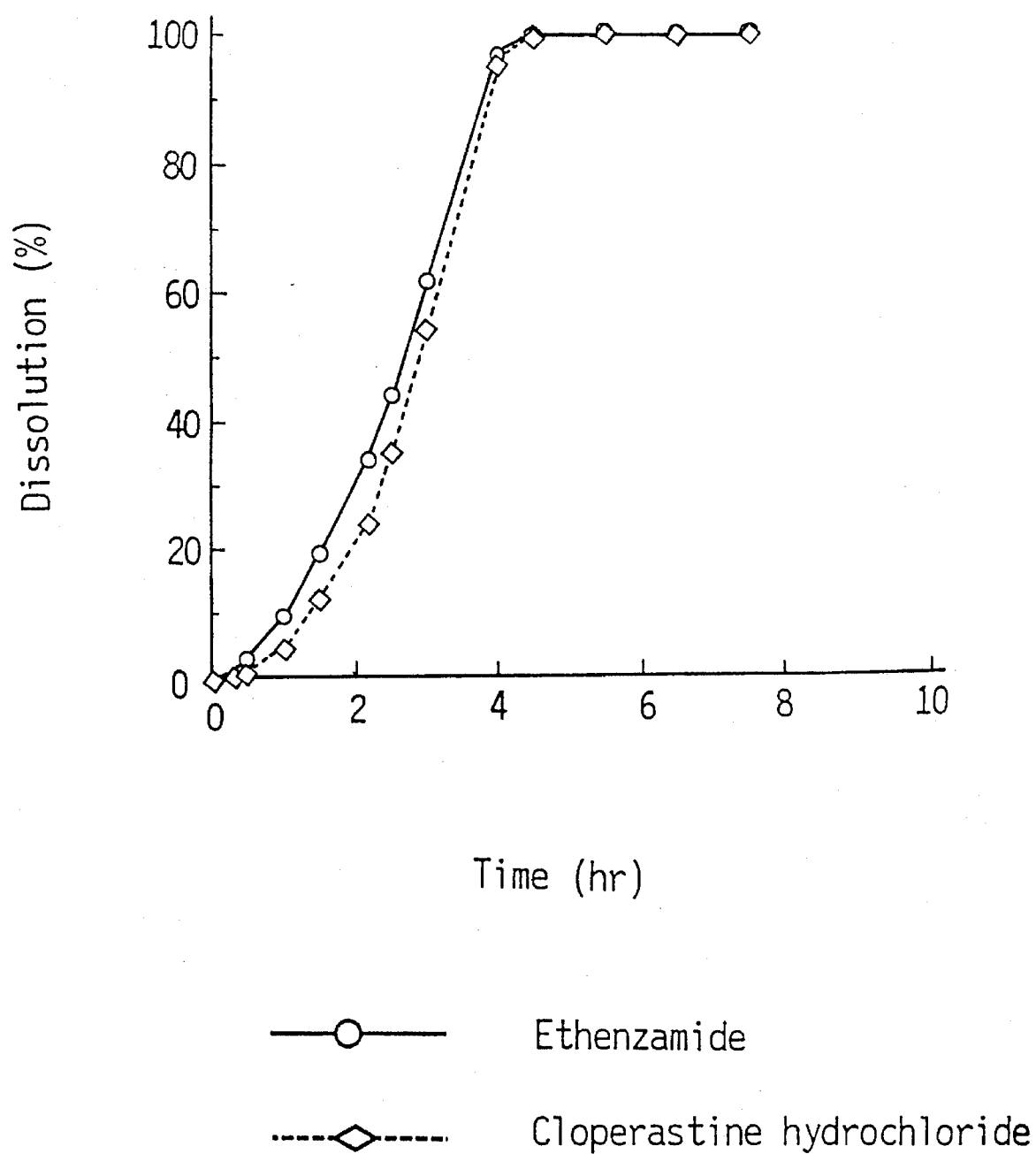
FIG. 9 is a graph showing the dissolution of the tablet of Example 4.

Using the same production method and the same dissolution test method as in Example 1, the dissolution test was conducted with water at 37° C. This example is concerned with the application to a mixture of a water-soluble drug and a slightly water-soluble drug. The water-soluble cloperastine chloride and slightly water-soluble ethenzamide both showed almost the same property of zero order dissolution (FIG. 9).

EXAMPLE 5

Figure 10:
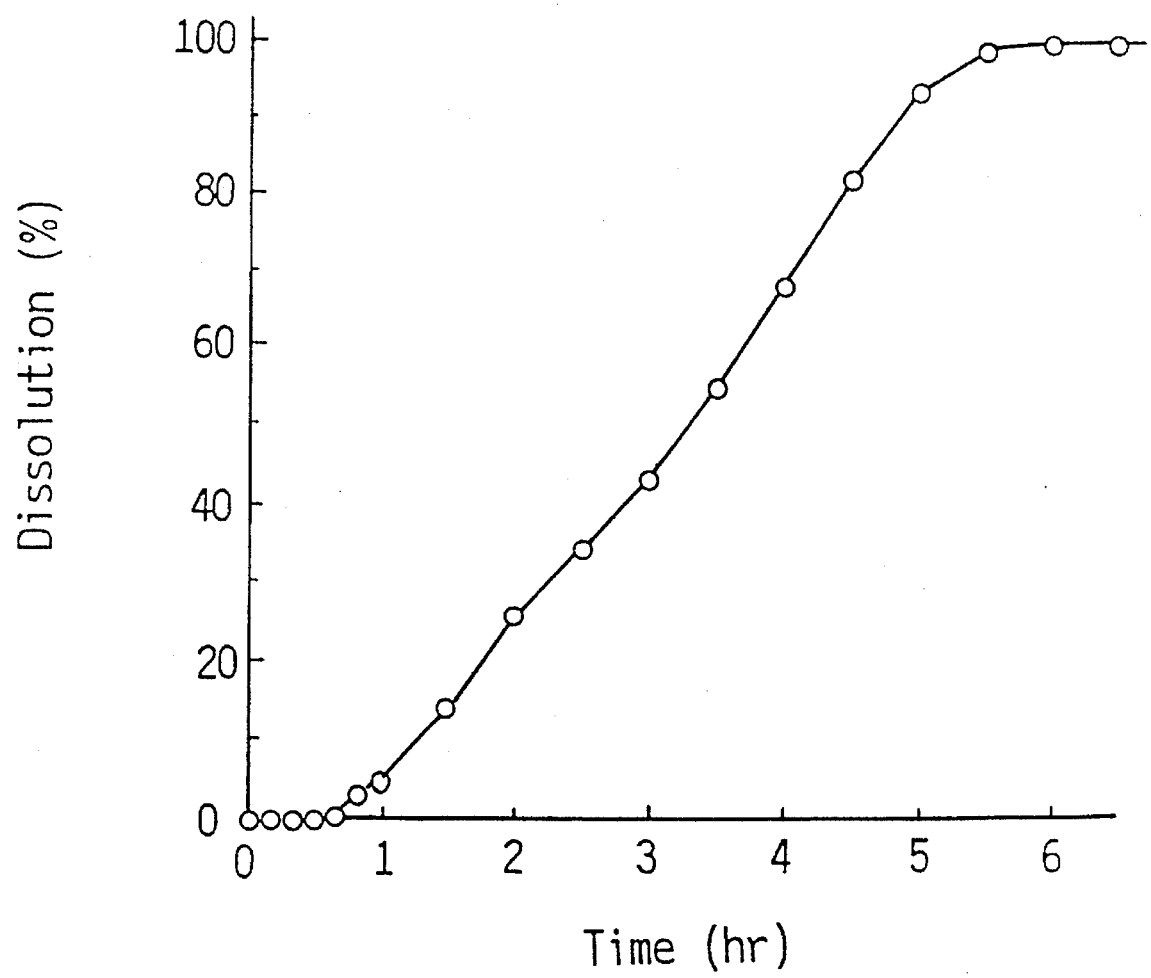
FIG. 10 is a graph showing the dissolution of the tablet of Example 5.

Phenylpropanolamine hydrochloride (187.5 g), Cellogen F (454 g), lactose (454 g) and magnesium stearate (4.5 g) were weighed, thoroughly mixed and directly compress-formed by a continuous compressor equipped with a 8 mm diameter, 6.5 R pounder under the main pressure of 1 ton into tablets each weighing 220 mg. Then, the obtained base tablets (1 kg) were placed in a pan coater (Freund Industry) and a solution of ETHOCEL 10 (90 g) and polyethylene glycol 6000 (42 g) in a mixture (2600 ml) of water-ethanol (1:9) was sprayed thereon until each tablet weighed 225 mg, followed by drying to give film coated tablets. The dissolution of phenylpropanolamine hydrochloride from this tablet was determined by the method of Example 1 using water at 37° C. The phenylpropanolamine hydrochloride showed almost complete zero order dissolution (FIG. 10).

EXAMPLE 6

Figure 11:
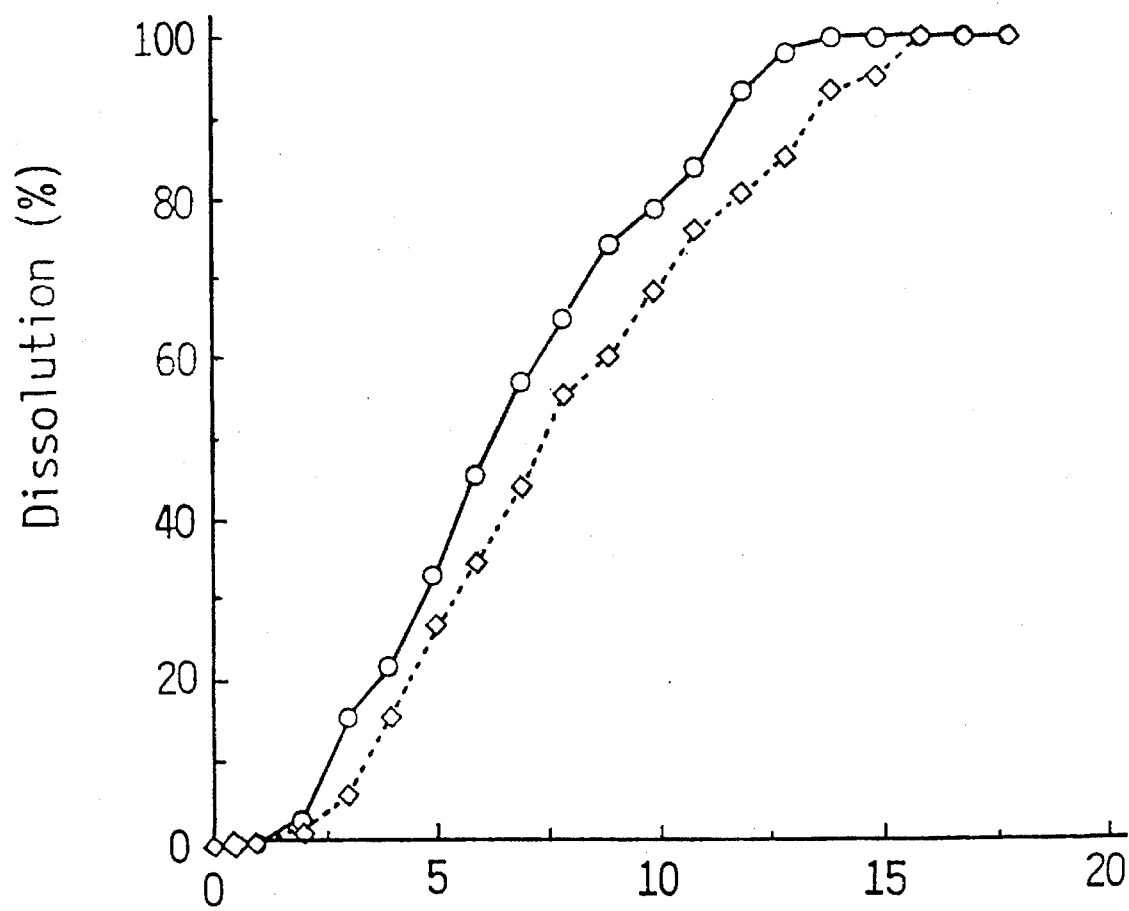
FIG. 11 is a graph showing the dissolution of the tablet of Example 6.

Phenylpropanolamine hydrochloride (181.5 g) passed through a 80 mesh sieve and Metolose 65SH1500 (757.5 g) were placed in a fluidized bed granulator and granulated by spraying a mixed solution of Eudragit NE30D-purified water (1:1) as a binder at 10 ml/min in such an amount as to allow Eudragit NE30D to be applied in a solid amount of 150 g, while blowing 60° C. air. Magnesium stearate (5 g) was mixed with the granules thus obtained and the mixture was directly compress-formed by a continuous compressor equipped with a 8 mm diameter, 6.5 R pounder under the main pressure of 1 ton into tablets each weighing 220 mg. Then, the obtained base tablets (1 kg) were placed in a pan coater (Freund Industry) and a solution of acetylcellulose (40 g) and AEA (40 g) in a mixture (1500 ml) of methylene chloride-ethanol (9:1) was sprayed thereon until each tablet weighed 225 mg, followed by drying to give film coated tablets. The dissolution of phenylpropanolamine hydrochloride from this tablet was determined by the method of Example 1 using 1st fluid (pH 1.2) and 2nd fluid (pH 6.8) at 37° C. No significant difference was found between the both solutions and the phenylpropanolamine hydrochloride showed almost complete zero order dissolution in the both solutions (FIG. 11).

EXAMPLE 7

Figure 12:
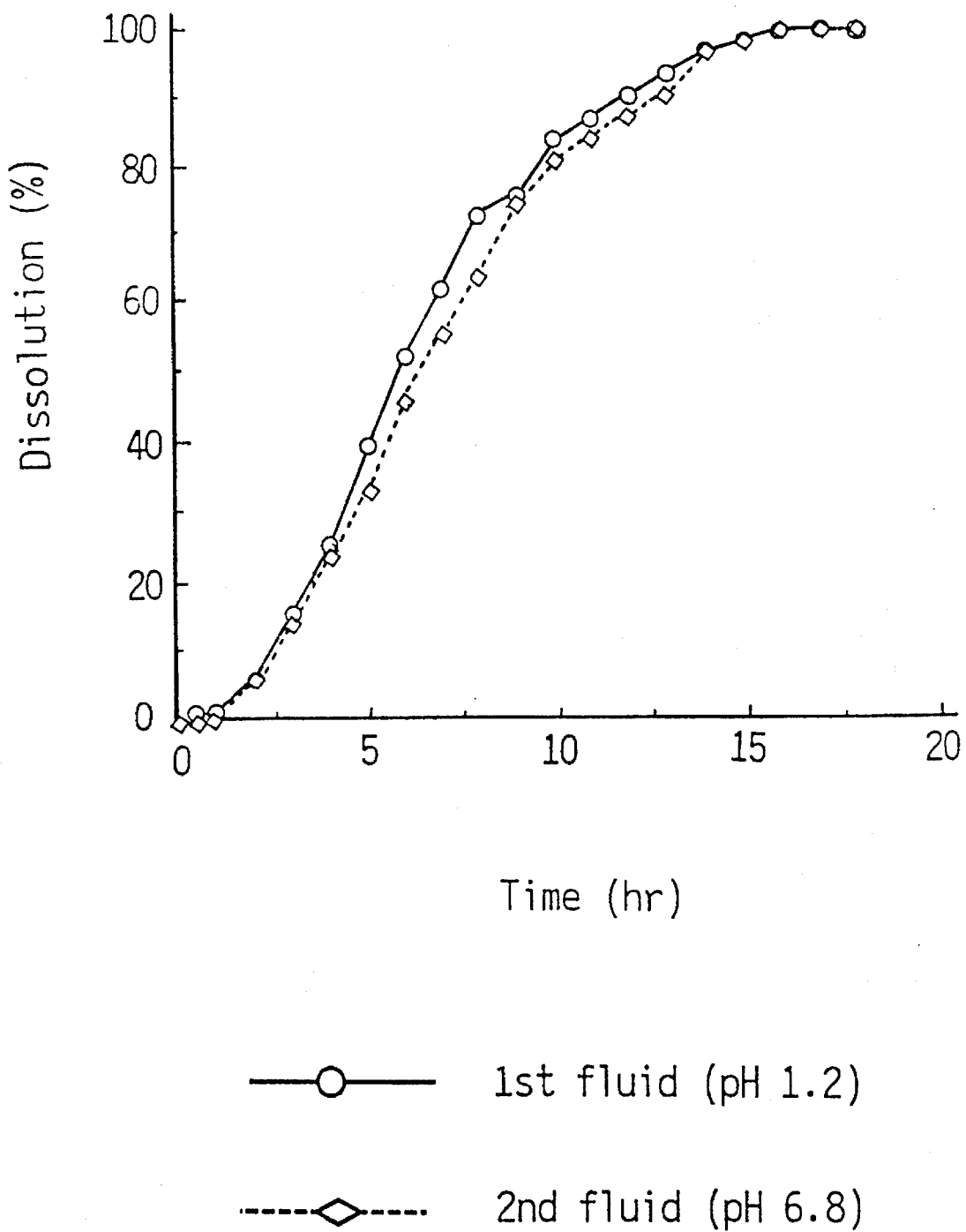
FIG. 12 is a graph showing the dissolution of the tablet of Example 7.

Phenylpropanolamine hydrochloride (187.5 g), Eudragit RS-PM (187.5 g), Metolose 60SH50 (195.5 g), Cellogen F (199.5 g), lactose (330 g) and magnesium stearate (4 g) were weighed, mixed, and directly compress-formed by a continuous compressor equipped with a 8 mm diameter, 6.5 R pounder under the main pressure of 1 ton into tablets each weighing 220 mg. Then, the obtained base tablets (1 kg) were placed in a pan coater (Freund Industry) and a solution of ETHOCEL 10 (60 g) in a mixture (1200 ml) of water-ethanol (1:9) was sprayed thereon until each tablet weighed 225 mg, followed by drying to give film coated tablets. The dissolution of phenylpropanolamine hydrochloride from this tablet was determined by the method of Example 1 using 1st fluid (pit 1.2) and 2nd fluid (pH 6.8) at 37° C. No significant difference was found between the both solutions and the phenylpropanolamine hydrochloride showed almost complete zero order dissolution (FIG. 12).

EXAMPLE 8

Phenylpropanolamine hydrochloride (300 g), Metolose 60SH50 (569.6 g) and polyethylene glycol 6000 (224 g) were weighed and mixed. A solution of HPC-L ethanol (5 w/v %, 448 ml) was added thereto and the mixture was kneaded, granulated and dried. Thereto was added magnesium stearate (4 g) and the mixture was compressed with a 6 mm diameter, 4.5 R pounder into tablets each weighing 70 mg. Then, the obtained tablets (800 g) were placed in a pan coater and a solution of ETHOCEL 10 (105 g) and polyethylene glycol (45 g) in ethanol (3000 ml) was sprayed thereon until each tablet weighed 80 mg, followed by drying to give core tablets.

Separately, phenylpropanolamine hydrochloride (100 g), lactose (2272 g), corn starch (800 g) and Avicel PH-101 (960 g) were weighed and mixed. An aqueous solution of HPC-L (5 w/v %, 1200 ml) was added thereto and the mixture was kneaded, granulated and dried. Thereto were added Avicel PH-101 (960 g) and magnesium stearate (25.6 g) to give a powder for the outer layer.

Figure 13:
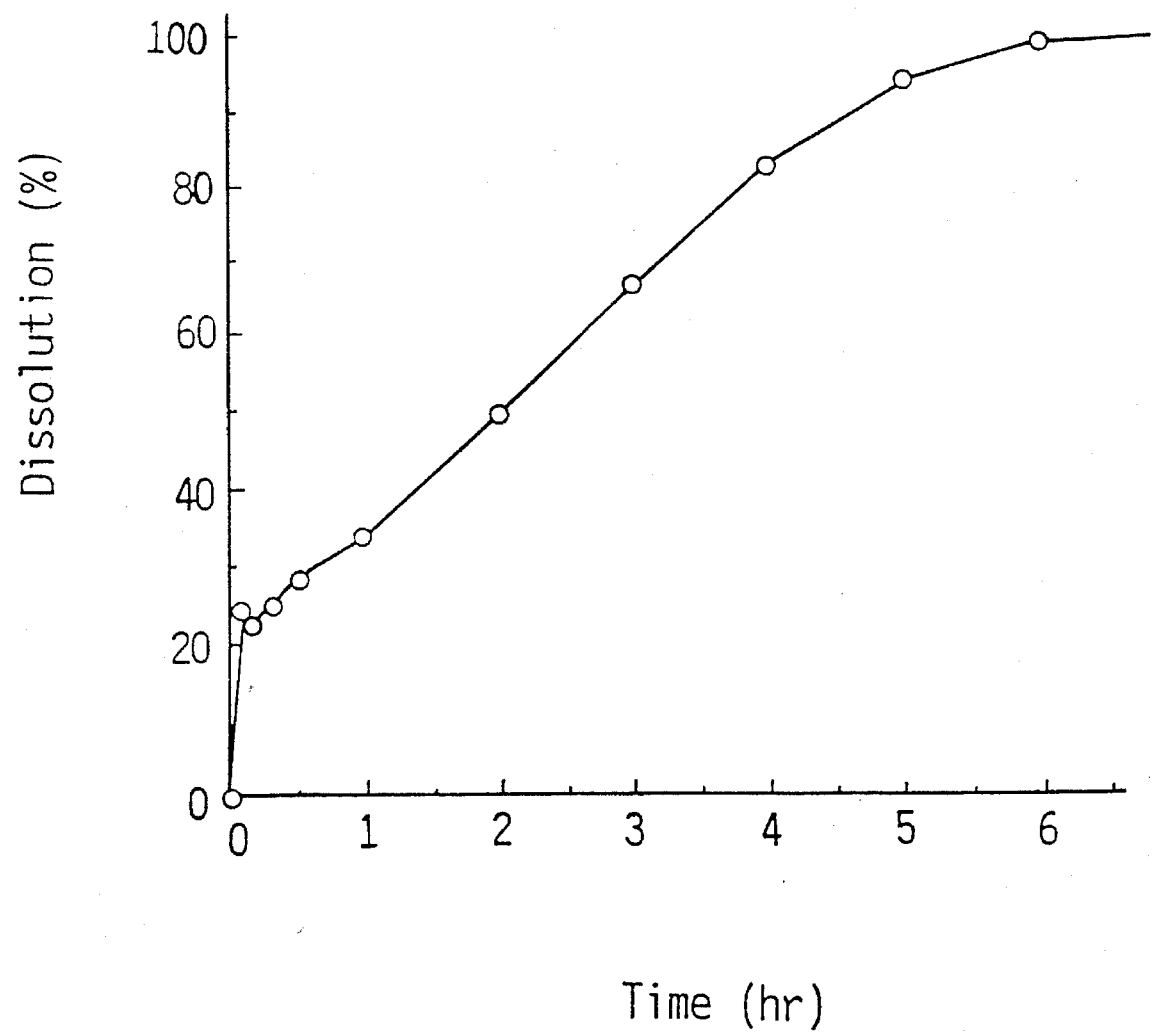
FIG. 13 is a graph showing the dissolution of the tablet of Example 8.

Using the aforementioned core tablets and the outer layer powder, dry coated tablets each weighing 403.6 mg were prepared. The dissolution of phenylpropanolamine hydrochloride from this tablet was determined by the method of Example 1 using water at 37° C. It was found that the rapid release portion was completely dissolved in 10 minutes, after which the sustained release portion showed almost complete zero order dissolution over the period of 7 hours (FIG. 13).

EXAMPLE 9

Figure 14:
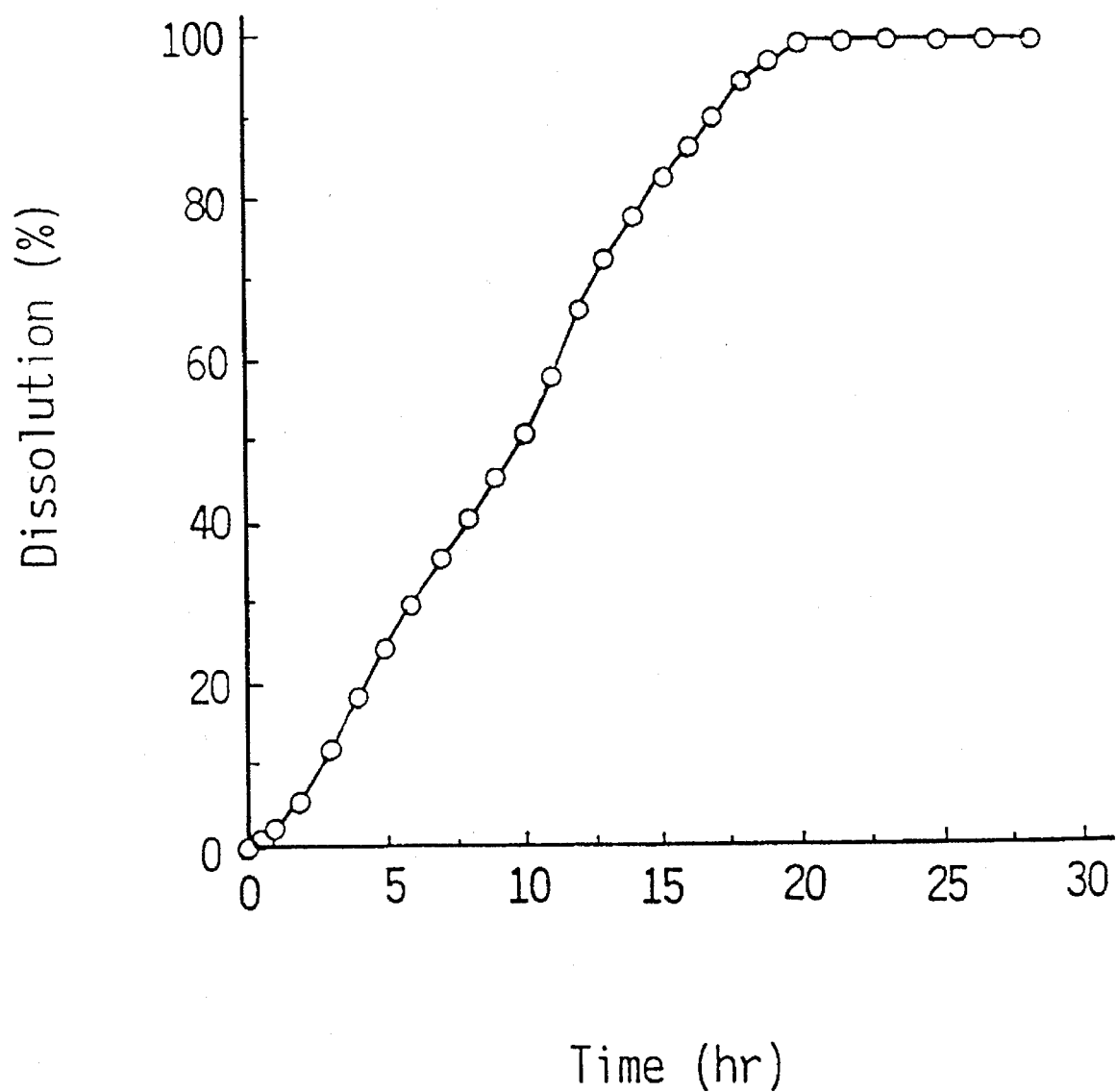
FIG. 14 is a graph showing the dissolution of the tablet of Example 9.

Pranoprofen (150.0 g), Metolose 60SH50 (124.0 g), corn starch (62.0 g), lactose (62.0 g) and magnesium stearate (1 g) were weighed and mixed. The mixture was directly compress-formed by a continuous compressor equipped with a 8 mm diameter, 6.5 R pounder into tablets each weighing 200 mg. Then, the obtained base tablets (1 kg) were placed in a pan coater (Freund industry) and a solution of ETHOCEL 10 (60 g) and polyethylene glycol 6000 (40 g) in a mixture (2000 ml) of water-ethanol (1:9) was sprayed thereon until each tablet weighed 210 mg, followed by drying to give film-coated tablets. The dissolution of pranoprofen from this tablet was determined by the method of Example 1 using 1st fluid (pH 1.2) at 37° C. There was found almost complete zero order dissolution over the period of 20 hours (FIG. 14.)

EXAMPLE 10

Figure 15:
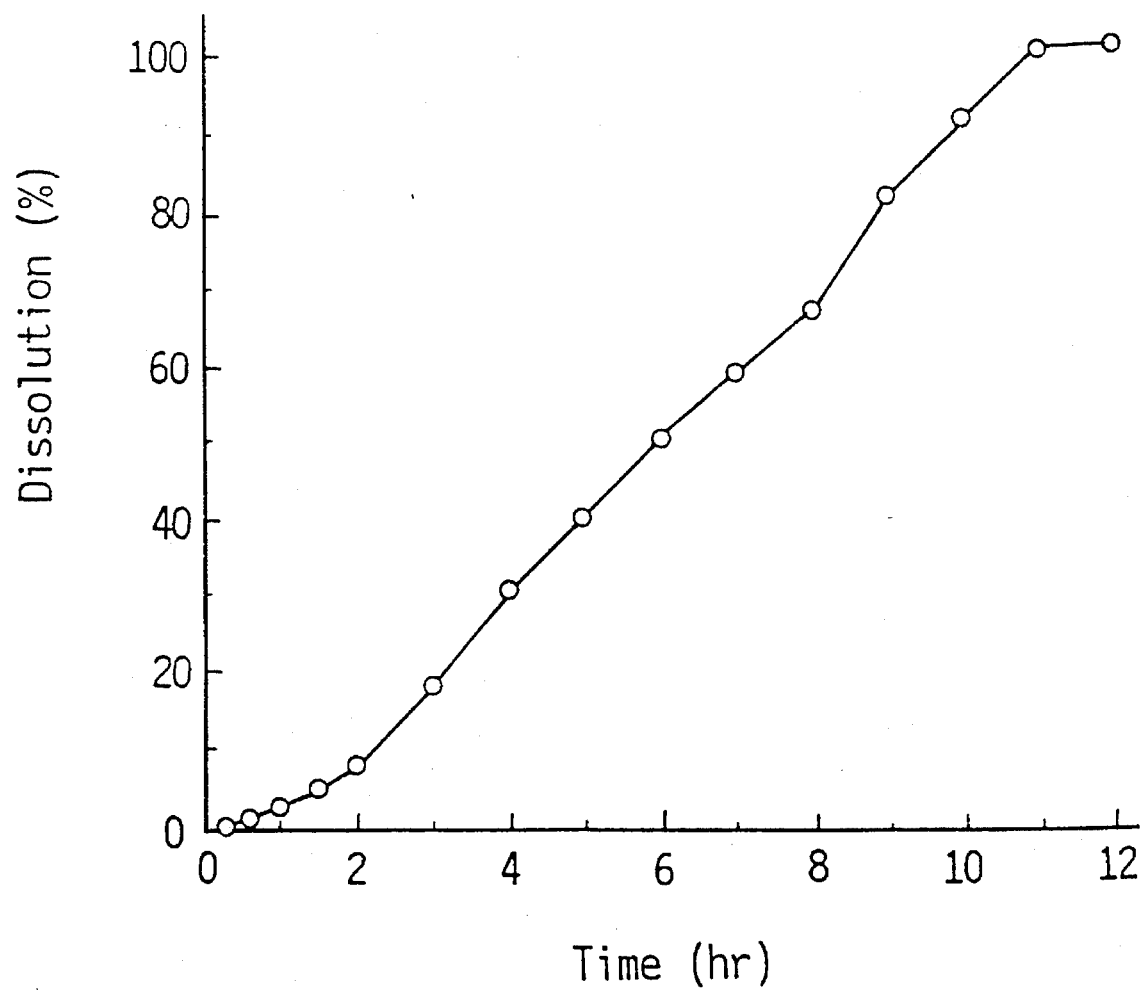
FIG. 15 is a graph showing the dissolution of the tablet of Example 10.

Pranoprofen (787.5 g), Metolose 65SH50 (775.5 g) and Metolose 65SH4000 (100 g) were mixed and granulated using a solution of HPC-L (25 g) in ethanol (1200 ml). The granules were left standing at 60° C. for 2 hours to dryness. After drying, the granules were passed through a 24 mesh sieve and mixed with magnesium stearate (12 g). The mixture was directly compress-formed by a continuous compressor equipped with a 7.5 mm diameter, 8.5 R pounder under the main pressure of 1.5 ton into tablets each weighing 170 mg. Then, the obtained base tablets (1 kg) was placed in a pan coater (Freund Industry) and a solution of ETHOCEL 10 (5.3 g), polyethylene glycol 4000 (1.3 g), Aerosil (1.3 g) and Avicel PH-F 20 (2.7 g) in a mixture (200 ml) of water:ethanol (1:24) was sprayed thereon and dried to give film coated tablets. The thickness of the film was about 0.004 mm at the side. The dissolution of pranoprofen from this tablet was determined by the method of Example 1 using 1st fluid (pH 1.2) at 37° C. There was found almost complete zero order dissolution over the period of 12 hours (FIG. 15.)

The thickness of each film obtained in Examples 1 through 9 is as follows.

|  | Top and bottom surfaces | Side surface |
| --- | --- | --- |
| Example 1 | about 0.011 mm | about 0.008 mm |
| Example 2 | about 0.036 mm | about 0.025 mm |
| Example 3 | about 0.032 mm | about 0.022 mm |
| Example 4 | about 0.035 mm | about 0.024 mm |
| Example 5 | about 0.010 mm | about 0.007 mm |
| Example 6 | about 0.009 mm | about 0.006 mm |
| Example 7 | about 0.010 mm | about 0.007 mm |
| Example 8 | about 0.038 mm | about 0.030 mm |
| Example 9 | about 0.019 mm | about 0.015 mm |

We claim:

1. A zero order dissolution sustained release tablet comprising a base tablet comprising a water-swellable gelling agent in a proportion of not less than 20% by weight per base tablet and a pharmaceutically active ingredient dispersed homogeneously in said gelling agent, said base tablet being coated with a film coating composition consisting essentially of one prepared by dissolving at least one member selected from the group consisting of ethylcellulose and acetylcellulose as a main component in an organic solvent, wherein the film coating composition is used in a proportion of 0.5–15% by weight relative to the base tablet, the thickness of the film is 0.002–0.05 mm at the side and 0.003–0.06 mm at the top or the bottom, and the ratio of the film thickness at the side to that at the top or the bottom is 0.55–0.85.

2. A zero order dissolution sustained release tablet comprising a base tablet comprising a water-swellable gelling agent in a proportion of not less than 20% by weight per base tablet and a pharmaceutically active ingredient dispersed homogeneously in said gelling agent, said base tablet being coated with a film coating composition consisting essentially of one prepared by dissolving at least one member selected from the group consisting of ethylcellulose and acetylcellulose, and polyethylene glycol in an organic solvent, wherein the film coating composition is used in a proportion of 0.5–15% by weight relative to the base tablet, the thickness of the film is 0.002–0.05 mm at the side and 0.003–0.06 mm at the top or the bottom, and the ratio of the film thickness at the side to that at the top or the bottom is 0.55–0.85.

3. The sustained release tablet of claim 1, wherein the water-swellable gelling agent is added in a proportion of 31.1–82.5% by weight per base tablet.

4. The sustained release tablet of claim 1, wherein the water-swellable gelling agent is one to three members selected from the group consisting of hydroxypropylcellulose, hydroxypropylmethylcellulose, sodium carboxymethylcellulose, aminoacrylmethacrylate copolymer RS and an emulsion of ethyl acrylate and methyl methacrylate copolymer.

5. The sustained release tablet of claim 1, wherein the water-swellable gelling agent is hydroxypropylmethylcellulose.

6. The sustained release tablet of any one of claims 1, 3, 4 and 5, wherein the pharmaceutically active ingredient is one or two members selected from the group consisting of phenylpropanolamine hydrochloride, acetaminophen, ethenzamide, cloperastine hydrochloride and pranoprofen.

7. The sustained release tablet of claim 2, wherein the water-swellable gelling agent is added in a proportion of 31.1–82.5% by weight per base tablet.

8. The sustained release tablet of claim 2, wherein the water-swellable gelling agent is one to three members selected from the group consisting of hydroxypropylcellulose, hydroxypropylmethylcellulose, sodium carboxymethylcellulose, aminoacrylmethacrylate copolymer RS and an emulsion of ethyl acrylate and methyl methacrylate copolymer.

9. The sustained release tablet of claim 2, wherein the water-swellable gelling agent is hydroxypropylmethylcellulose.

10. The sustained release tablet of any one of claims 2, 7, 8 and 9, wherein the pharmaceutically active ingredient is one or two members selected from the group consisting of phenylpropanolamine hydrochloride, acetaminophen, ethenzamide, cloperastine hydrochloride and pranoprofen.

\* \* \* \* \*